United States Patent [19]
Murphy

[11] Patent Number: 5,686,098
[45] Date of Patent: Nov. 11, 1997

[54] ACTIVE SUBSTANCE PATCH FOR THE RELEASE OF ESTRADIOL TO THE SKIN

[75] Inventor: Teresa Marie Murphy, Gwent, United Kingdom

[73] Assignee: LTS Lohmann Therapie-Systeme GmbH, Neuwied, Germany

[21] Appl. No.: 530,107

[22] PCT Filed: Mar. 7, 1994

[86] PCT No.: PCT/EP94/00670

§ 371 Date: Feb. 12, 1996

§ 102(e) Date: Feb. 12, 1996

[87] PCT Pub. No.: WO94/22481

PCT Pub. Date: Oct. 13, 1994

[30] Foreign Application Priority Data

Mar. 26, 1993 [DE] Germany ............... 43 09 830.4

[51] Int. Cl.$^6$ ........................................ A61F 13/02
[52] U.S. Cl. ................. 424/448; 424/449; 514/946; 514/947
[58] Field of Search ................... 424/448, 449; 514/946, 947

[56] References Cited

U.S. PATENT DOCUMENTS

| | | | |
|---|---|---|---|
| 4,746,515 | 5/1988 | Cheng et al. | 424/449 |
| 4,818,540 | 4/1989 | Chien | 424/448 |
| 4,906,169 | 3/1990 | Chien | 424/448 |
| 5,023,084 | 6/1991 | Chien | 424/448 |
| 5,120,546 | 6/1992 | Hansen | 424/449 |

FOREIGN PATENT DOCUMENTS

| | | |
|---|---|---|
| 0 356 382 | 2/1990 | European Pat. Off. . |
| 2 306 311 | 8/1973 | Germany . |
| 1 385 914 | 10/1972 | United Kingdom . |
| 91/05529 | 5/1991 | WIPO . |

*Primary Examiner*—Gabrielle Phelan
*Attorney, Agent, or Firm*—Wenderoth, Lind & Ponack

[57] ABSTRACT

An active substance patch releasing estradiol to the skin is characterized by the fact that it consists essentially of a backing layer and an attached active substance reservoir which comprises pressure sensitive adhesive and in which the active substance is at least partially soluble, and of a removable protective layer covering the adhesive film, the active substance reservoir being a polymer matrix which—in order to improve the bioavailability of the estradiol—comprises an added penetration enhancer of the general formula:

$$\begin{array}{c} CH_2\text{——}CH\text{—}R \\ | \quad\quad\quad | \\ O \quad\quad\quad O \\ \diagdown \diagup \\ C \\ \diagup \quad \diagdown \\ CH_3 \quad CH_3 \end{array}$$

wherein
$R = \text{—}CH_2OH$ or $\text{—}CH_2\text{—}O\text{—}CH_2\text{—}CHOH\text{—}CH_2OH$.

8 Claims, 1 Drawing Sheet

ACTIVE SUBSTANCE PATCH FOR THE RELEASE OF ESTRADIOL TO THE SKIN

This application is a 371 of PCT/EP94/00670, filed Mar. 7, 1994.

The present invention relates to an active substance patch for the release of estradiol to the skin consisting essentially of a backing layer, an active substance reservoir which is connected to the backing layer, and which comprises a pressure sensitive adhesive and wherein the active substance is at least partially soluble, and a removable protective layer covering the adhesive film.

Estradiol is required to alleviate the symptoms of menopause, oophorectomy and primary pituitary failure. For this reason there is a significant need for an estradiol replacement therapy for alleviating both menopausal symptoms, such as hot flushes, nervous discomfort, or disturbed sleep, and osteoporosis (loss of bone mass) and atherosclerosis accompanying estradiol deficiency.

When estradiol, in particular 17-β-estradiol, is administered orally, the absorption is unsatisfactory because of its low water-solubility after oral administration. Due to the rapid metabolism of 17-β-estradiol through the liver high doses are required, frequently resulting in undesired side effects, such as sickness and thrombo-embolism. Therefore it is necessary to improve the means and methods of the estradiol therapy.

The transdermal route of parenteral administration allows the administration of lower doses of 17-β-estradiol in order to avoid the first-pass-metabolism. With this administration form the metabolism of relatively large amounts of estradiol is avoided.

Thus, the transdermal route offers advantages over other routes. Transdermal systems for the administration of a large variety of different active substances or other medicinal agents are exemplified in U.S. Pat. Nos.: 4,906,169; 5,023,084; 4,818,540 and 4,746,515 and in WO 91/05529. With respect to their size, thickness and active substance utilization, the transdermal systems according to the state of the art are not satisfactory since only a small portion of the applied dose is utilized therapeutically. Despite the developments made in the modes of administration, there is a need for further improved techniques to provide the users of said drug with another constant estradiol level in a favorable, i.e. transdermally applicable, mode of dosage. In principle it is known to apply estradiol transdermally, however, for the above reasons it is desirable to develop improved transdermal processes for the administration of estradiol.

It is the object of the present invention to provide an active substance patch for releasing estradiol to the skin, which has a pressure sensitive adhesive-containing active substance reservoir in which the active substance is at least partially soluble and which delivers therapeutically effective estradiol rates at an increased bioavailability as compared to the oral or intramuscular administration of the active substance. The active substance patch is to provide a favorable therapy with an improved compliance, in particular owing to its advantageous mode of dosage.

In an active substance patch of the kind described herein this object is achieved according to the present invention by the fact that the active substance reservoir is a polymer matrix to which—in order to improve the bioavailability of the estradiol—a penetration enhancer of the general formula

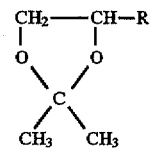

is added, in which
R=—CH$_2$OH or —CH$_2$—O—CH$_2$—CHOH—CH$_2$OH,
corresponding to the compounds monoisopropylidene glycerol (MIPG) or monoisopropylidene diglycerol (MIPD).

By adding the penetration enhancer according to the invention the bioavailability of the active substance is considerably improved to advantage, allowing the application of a lower active substance dose as compared to known systems. The active substance patch prepared according to the present invention provides the required estradiol dose from a transdermal system.

According to one embodiment of the present invention the active substance patch additionally comprises one or more other compounds further intensifying the action of the penetration improving agent.

For example, it is provided that these penetration-supporting compounds be selected from the group consisting of polyethylene glycols, glycols and/or pyrrolidones and/or polymers of pyrrolidone derivatives, for example Kollidon® 25 (BASF, homopolymer of N-vinyl-2-pyrrolidone). Compounds of the first-mentioned groups, for example, include propylene glycol (PG), 2-pyrrolidone (2-P), and polyethylene glycol 400 (PEG 400).

According to another embodiment it is provided that the active substance-containing reservoir comprises homo and/or copolymers of acrylates and/or methacrylates.

Additionally, the active substance-containing reservoir may comprise up to 3% by weight of a filler. The concentration of estradiol in the reservoir advantageously amounts to 0.7–3.5% by weight.

In this connection the weight ratio between estradiol and penetration accelerator may amount to 1:3 to 1:15.

According to another embodiment it is provided that the active substance-containing reservoir comprises up to 5% by weight of a water-absorbing polymer.

It has proven to be advantageous that the estradiol is 17-β-estradiol.

The present invention utilizes the principles of the transdermal active substance release to the organism via the skin and is directed to the administration of estradiol.

Embodiments of the present invention employ a backing layer, which may be manufactured from a suitable material which is impermeable to the active substance and to other components of the reservoir layer. This backing layer fulfils the required protective and supportive function. Suitable materials used for the backing layer may be polyester, polyvinyl chloride, polyamide, polyethylene, polypropylene, and polyurethane, as well as composites of these materials. Metal foils, e.g. of aluminum, may also be used, either alone or laminated with a polymeric substance. An active substance-containing polymer matrix manufactured according to the present invention comprises the active substance distributed in a pressure sensitive adhesive base substance; said base substance may, for instance, be based on polyacrylates or polymethacrylates, polyurethanes, silicones, polyisobutylenes, polysiloxanes, or styrene-isoprene-styrene-copolymers, and on copolymers of ethylene with vinyl acetate or acrylic acid derivatives. In this manner it is ensured that the active substance is in close contact with the skin.

The mentioned enhancers may be used individually or in combination. They are distributed over the whole pressure sensitive adhesive matrix comprising the active substance.

The pressure sensitive adhesive matrix is laminated on a suitable removable protective layer. A protective layer suitable for such laminates consists of the same materials as those described for the backing layer; however they have been rendered removable by conventional siliconization. Further removable protective layers may consist of polyethylene laminated with an aluminum foil, the polyethylene side provided with the pressure sensitive adhesive matrix being siliconized; other protective layers consist of polytetrafluoroethylene, pretreated paper, cellophane and the like.

Manufacture of the system

BRIEF DESCRIPTION OF THE DRAWING

The preferred embodiment of the present invention is illustrated in FIGURE 1 representing a cross section of the TTS according to the invention. In this FIGURE 1 (1) represents the backing layer, (2) the reservoir comprising the active substance and the enhancer, and (3) the removable protective layer.

The active substance-comprising reservoir may be formed of polymers of acrylates and methacrylates. The active substance-containing reservoir may also comprise a water-absorbing polymer, e.g. a homopolymer of N-vinyl-2-pyrrolidone, as well as fillers, such as Aerosil® or Syloid®.

Figure 1:
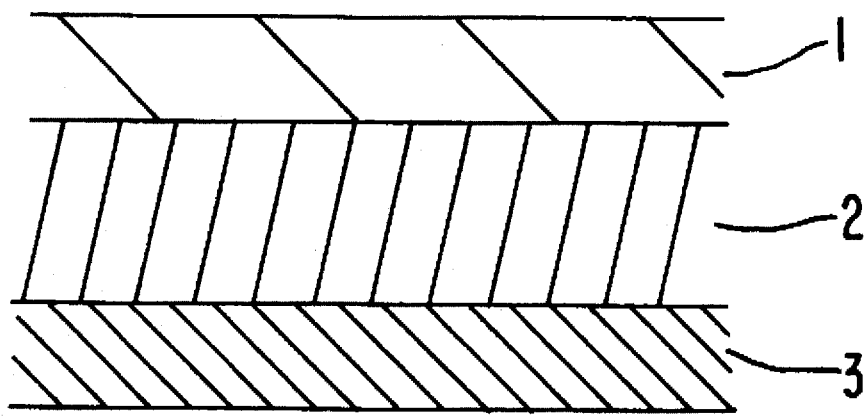

The proportion of the incorporated filler may range between 1 and 3%-wt., preferably between 1.5 and 2%-wt.

The proportion of the incorporated water-absorbing polymer may amount to up to 5%-wt.

The active substance and the enhancer(s) are combined with each other at different proportions ranging between 1:3 and 1:15, and they are incorporated either by dissolution or dispersion of the active substance-enhancer-combination in a polyacrylate solution. The resulting mixture is stirred until a homogeneous dispersion results. The resultant flowable preparation is distributed on a surface and the solvent evaporated so that a solvent-free matrix is obtained comprising the active substance and the enhancer. This matrix is in the form of a film.

A typical embodiment of the present invention comprises between 0.7% and 3.5% 17-β-estradiol (based on percent by weight of the film) and between 8%-wt. and 28%-wt. enhancer.

The following examples illustrate the realization of the present invention in a transdermal system of the matrix type, in which the administration of the active substance is effected through the monolithic or laminated matrix system in a diffusion-controlled manner. In addition, the present invention may also be used in the membrane type wherein the active substance diffusion from the reservoir is controlled by the membrane, the reservoir being filled with a liquid or a semisolid substance.

EXAMPLES

Examples 1–6

According to the present invention monolithic matrix systems were manufactured as follows: The enhancer(s) was/were intensely mixed with the active substance and silicon dioxide filler (by Grace GmbH) and/or the water-absorbing polymer Kollidon® 25 (by BASF). A solution of the polyacrylate pressure sensitive adhesive (Durotak 280-2516, by National Starch) was added thereto, typical solvents for the polymer comprising lower alcohols, such as ethanol and methanol, lower alkane esters, such as ethyl acetate, and alkanes, such as heptane. This mixture was stirred until a homogeneous mass formed. This adhesive mass was allowed to stand for 15 min. and then spread on a siliconized polyester sheet (Hostaphan RN 100) at a thickness of 200 µm, the solvent was removed by drying in an oven at 50° C. The resultant solvent-free matrix was laminated with a polyester backing layer (Hostaphan RN 15). Patches of 2.54 cm$^2$ in size were cut from this laminate and assessed by in-vitro-skin-permeation-studies.

The siliconized protective layer was removed and the backing layer with the adhering active substance-containing matrix pressed to the stratum-corneum-side of excized naked mice skin. Then, the skin together with the attached system was introduced into a Franz-diffusion-cell. The receiver medium, which comprised 40% polyethylene glycol in water, was stirred and. Constantly kept at a temperature of 37° C. At predetermined time intervals samples were taken out and the volumes were immediately replaced by fresh receiver liquid which had previously been brought into an equilibrium state. The samples were examined by HPLC. The active substance flux was determined by the gradient of the active substance amount present in cumulated form in the receptor medium, which was put in relation to time. The flux values of Examples 1–6 are listed in Table 1. All systems listed in Table 1 had acceptable flux values, however, the best results were achieved when MIPD was used alone.

Example 7

Monolithic matrix systems were manufactured according to the invention and used with excised naked guinea pig skin. In-vitro-permeation-experiments were carried out to determine the bioequivalence of the different systems. The commercial transdermal system Estraderm-25 TTS was used as standard. In order to compare the bioequivalence of the systems, the flux values were expressed as percentage of the applied dose. The data is listed in Table 2.

The results show that the best bioequivalence was obtained with a monolithic matrix system comprising MIPD as penetration enhancer. Although this enhancer can act in the same manner as ethanol in the Estraderm-TTS, i.e. as a solvent for the active substance, a surprisingly high flux was achieved in this monolithic system. In this manner it is possible to reduce the size of the TTS (to approximately 4 cm$^2$) and still release therapeutically effective estradiol doses (50 µg within 24 hours).

Example 8

If the MIPD is replaced by MIPG comparable results are obtained.

TABLE 1

In vitro flux of estradiol through naked mice skin

(per cent by weight of the solvent-free matrix)

| Example | Polyacrylate | SiO$_2$ | PG | Estradiol | MIPD | 2-P | PEG 400 | Flux ($\mu g\ cm^{-2}h^{-1}$) |
|---|---|---|---|---|---|---|---|---|
| 1 | 70 | 1.2 | 12 | 1.8 | 15 | / | / | 0.523 ± 0.01 |
| 2 | 70 | 1.2 | 15 | 1.8 | 12 | / | / | 0.523 ± 0.13 |
| 3 | 70 | 1.2 | / | 1.8 | 12 | 15 | / | 0.500 ± 0.03 |
| 4 | 70 | 1.2 | / | 1.8 | 12 | / | 15 | 0.397 ± 0.04 |
| 5 | 70 | 1.2 | 17 | 1.8 | 10 | / | / | 0.523 ± 0.08 |
| 6 | 70 | 2.65 | / | 1.8 | 25.6 | / | / | 0.612 ± 0.09 |

TABLE 2

In vitro flux of estradiol through naked guinea pig skin

(per cent by weight of the solvent-free matrix)

| Example | Polyacrylate | SiO$_2$ | PG | Estradiol | MIPD | Kollidon-25 | Flux (%/h) |
|---|---|---|---|---|---|---|---|
| 7 | 70 | 1.2 | 15 | 1.8 | 12 | / | 12.56 |
| 8 | 70 | 2.65 | / | 1.8 | 25.6 | / | 18.36 |
| 9 | 82.9 | / | / | 2.7 | 10.1 | 4.2 | 21.61 |
| Estraderm.25 TTS (= prior art) | | | | | | | 4.24* |

*calculated from the flux indicated in WO 91/05529

I claim:

1. An active substance patch for the release of estradiol to the skin consisting essentially of a backing layer and an active substance reservoir connected thereto which comprises estradiol and a pressure sensitive adhesive and in which the estradiol is at least partially soluble, and a removable protective layer covering the adhesive film, wherein the active substance reservoir is a polymer matrix to which, in order to improve the bioavailability of the estradiol, a penetration enhancer of the formula

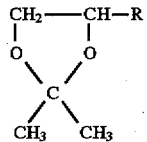

is added, wherein
R=—CH$_2$OH or —CH$_2$—O—CH$_2$—CHOH—CH$_2$OH,
the weight ratio of estradiol to penetration enhancer being 1:3 to 1:15.

2. The active substance patch according to claim 1 wherein the active substance-containing reservoir comprises up to 3%-wt. of a filler.

3. The active substance patch according to claim 1 wherein the concentration of estradiol in the reservoir amounts to 0.7 to 3.5%-wt.

4. The active substance patch according to claim 1 wherein the active substance-containing reservoir comprises up to 5%-wt. of a water-absorbing polymer.

5. The active substance patch according to claim 1 wherein the estradiol is 17-β-estradiol.

6. The active substance patch according to claim 1 wherein the active substance reservoir additionally comprises at least one compound intensifying the action of the penetration enhancer.

7. The active substance patch according to claim 6 wherein additional penetration enhancing compounds are selected from the group consisting of polyethylene glycols, glycols, pyrrolidones, vinyl pyrrolidone polymers and mixtures thereof.

8. The active substance patch according to claim 1 wherein the active substance-containing reservoir comprises homopolymers or copolymers of an acrylate or methacrylate or mixtures thereof.

* * * * *